United States Patent [19]

Weyer et al.

[11] Patent Number: 6,162,939
[45] Date of Patent: Dec. 19, 2000

[54] METHOD FOR PRODUCING THIOCHLOROFORMATES

[75] Inventors: Hans-Jürgen Weyer, Bobenheim-Roxheim; Armin Stamm, Mainz; Theodor Weber, Ludwigshafen; Jochem Henkelmann, Mannheim, all of Germany

[73] Assignee: BASF Aktiengesellschaft, Ludwigshafen, Germany

[21] Appl. No.: 09/485,842

[22] PCT Filed: Aug. 28, 1998

[86] PCT No.: PCT/EP98/05525

§ 371 Date: Feb. 17, 2000

§ 102(e) Date: Feb. 17, 2000

[87] PCT Pub. No.: WO99/11611

PCT Pub. Date: Mar. 11, 1999

[30]  Foreign Application Priority Data

Aug. 28, 1997 [DE]  Germany ............................. 197 37 619

[51] Int. Cl.$^7$ ......................... C07C 327/22; C07C 327/20
[52] U.S. Cl. ............................................. 558/250; 558/257
[58] Field of Search ...................................... 558/250, 257

[56]  References Cited

U.S. PATENT DOCUMENTS

| | | | |
|---|---|---|---|
| 3,277,143 | 10/1966 | Tilles | ........................................ 558/249 |
| 4,340,746 | 7/1982 | Semler et al. | ........................ 558/249 X |
| 4,400,329 | 8/1983 | Deweerdt et al. | ........................ 558/249 |

FOREIGN PATENT DOCUMENTS

| | | |
|---|---|---|
| 0 024 683 | 3/1981 | European Pat. Off. . |
| 0 053 981 | 6/1982 | European Pat. Off. . |
| 0 309 844 | 4/1989 | European Pat. Off. . |

*Primary Examiner*—Michael G. Ambrose
*Attorney, Agent, or Firm*—Keil & Weinkauf

[57]  ABSTRACT

A catalyst used for preparing thiochloroformates by reacting thiols with phosgene is a cyclic urea or cyclic thiourea which may be in the form of a salt obtainable by reaction with a hydrohalic acid or phosgene.

9 Claims, No Drawings

METHOD FOR PRODUCING THIOCHLOROFORMATES

The invention relates to a process for preparing thiochloroformates by reacting thiols with phosgene in the presence of a catalyst.

Thiochloroformates are important intermediates in organic synthesis, in particular of physiological active substances such as drugs and crop protection agents. Thiochloroformates are obtained by reacting thiols with phosgene in a process which has been known for a long time. Since the reaction of thiols with phosgene takes place very slowly and with considerable formation of byproducts such as thiocarbonates and disulfides, it is normally carried out in the presence of catalysts.

U.S. Pat. No. 3,299,114 discloses the preparation of thiochloroformates by phosgenation of the corresponding thiols (mercaptans), using as catalysts open-chain or heterocyclic tertiary amines or heterocyclic aromatic nitrogen bases of the pyridine type. However, the yields of thiochloroformates obtained thereby are unsatisfactory.

EP-A 0 024 683 and EP-A 0 053 981 propose carboxamides and acyclic ureas as catalysts. The disadvantages of these processes are that the yields are still unsatisfactory, the amount of byproducts is high, and the catalyst content of the mixtures from the synthesis is high. It is therefore necessary for the thiochloroformates which have been formed to be worked up in another process step, as a rule by distillation.

DE-A 41 37 012 discloses organic phosphorus compounds as catalysts for preparing thiochloroformates. The disadvantage of these processes is that distillation residues containing phosphorus are produced and are difficult to dispose of because of the formation of phosphonic acids on incineration.

It is an object of the present invention to remedy the abovementioned disadvantages, in particular to provide a process for preparing thiochloroformates, which makes do with very small amounts of catalyst and substantially avoids the formation of byproducts.

We have found that this object is achieved by a process for preparing thiochloroformates from thiols by reaction with phosgene (phosgenation) in the presence of a catalyst, wherein a cyclic urea or thiourea is used as catalyst. By cyclic ureas or thioureas are meant those compounds in which the urea or thiourea moiety is part of a ring system. The cyclic urea or thiourea may be present either as such or in the form of its salts which are obtainable by reaction with hydrohalic acids or phosgene.

Cyclic ureas or thioureas are known per se. Their preparation is described, for example, in Houben-Weyl, Methoden der organischen Chemie, Volume E4, 4th edition, 1983. Particularly suitable catalysts are cyclic ureas or thioureas of the formula I:

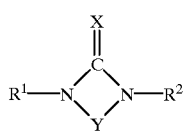

(I)

where

X is an oxygen or sulfur atom,

Y is a saturated of mono- or polyolefinically unsaturated carbon chain which has 2 to 8 carbon atoms and which is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and cyano and which may contain an ether, thioether, tertiary amino, keto, lactone, alkyl-substituted lactam, sulfone or diketo moiety, or is a cycloalkylene having 5 to 12 carbon atoms, heterocycloalkylene group having 4 to 11 carbon atoms, arylene group having 6 to 12 carbon atoms or hetarylene group having 3 to 11 carbon atoms, each of which is unsubstituted or mono- to trisubstituted by $C_1$–$C_4$-alkyl, $C_1$–$C_4$-alkoxy, phenoxy, $C_2$–$C_4$-acyl, $C_2$–$C_4$-acyloxy, $C_2$–$C_8$-dialkylamino, halogen, nitro and/or cyano, and $R^1$ and $R^2$, which may be identical or different, are $C_1$–$C_{20}$-alkyl, $C_2$–$C_{20}$-alkenyl or $C_2$–$C_{20}$-alkynyl, each of which is unsubstituted or mono- to trisubstituted by $C_1$–$C_4$-alkoxy, $C_2$–$C_4$-acyl, $C_2$–$C_4$-acyloxy, $C_2$–$C_8$-dialkylamino, halogen, nitro and/or cyano, or is $C_2$–$C_{20}$-acyl or is $C_3$–$C_8$-cycloalkyl, $C_4$–$C_{20}$-cycloalkylalkyl, $C_3$–$C_8$-heterocycloalkyl, $C_4$–$C_{20}$-heterocycloalkylalkyl, $C_6$–$C_{14}$-aryl or $C_7$–$C_{20}$-arylalkyl, each of which is unsubstituted or mono- to trisubstituted by $C_1$–$C_4$-alkyl, $C_1$–$C_4$-alkoxy, $C_2$–$C_4$-acyl, $C_2$–$C_4$-acyloxy, $C_2$–$C_8$-dialkylamino, halogen, nitro and/or cyano, or $R^1$ and $R^2$ are part of a mono- or polyolefinically unsaturated carbon chain having 2 to 8 carbon atoms, a cycloalkylene group having 5 to 12 carbon atoms, heterocycloalkylene group having 4 to 11 carbon atoms, arylene group having 6 to 12 carbon atoms or hetarylene group having 3 to 11 carbon atoms, which in each case connects the two nitrogen atoms.

Y is a saturated or a mono- or polyunsaturated carbon chain having 2 to 8 carbon atoms such as $C_2$–$C_8$-alkylene, $C_2$–$C_8$-alkenylene, $C_4$–$C_8$-alkadienylene or $C_6$–$C_8$-alkatrienylene. Examples are ethylene, propylene, butylene, penlylene, hexylene, heptylene, octylene, vinylene, propenylene, 1-butenylene, 2-butenylene, butadienylene, 1-pentenylene, 1,3-pentadienylene, 1,4-pentadienylene, 1-hexenylene, 1,3-hexadienylene and 1,3,5-hexatrienylene, preferably ethylene, propylene and vinylene. The carbon chain may also contain groups which are inert toward phosgene and thiol under the reaction conditions, such as an ether, thioether, tertiary amino, keto, lactone, substituted lactone, sulfone or α-diketo moiety, and in the case of a $C_2$ chain Y may also consist exclusively of an α-diketo moiety.

Y may furthermore be a (divalent) cycloalkylene group which his 5 to 12 carbon atoms and may be bonded by vicinal carbon atoms or in the 1,3 position. Examples are 1,2- or 1,3-cyclopentylene, 1,2- or 1,3-cyclohexylene and 1,2- or 1,3-cycloheptylene. The cycloalkylene group may also contain one or more heteroatoms such as nitrogen, oxygen or sulfur in place of one or more carbon atoms. Y may furthermore be a (divalent) arylene group which has 6 to 12 carbon atoms and is bonded by vicinal carbon atoms. Examples are ortho-phenylene, 1,2- or 2,3-naphthylene, and 1,2- or 2,3-anthracenylene, preferably ortho-phenylene. The arylene group may also contain one or more heteroatoms such as nitrogen in place of one or more carbon atoms. Examples are 2,3- or 3,4-pyrrolylene, 2,3- or 3,4-pyridinylene, 2,3-, 3,4-, 5,6- or 6,7-quinolinylene or 2,3-, 5,6- or 6,7-quinoxalinylene.

The groups mentioned above for Y may furthermore be mono- to trisubstituted by groups which are inert toward phosgene and thiol under the reaction conditions, such as $C_1$–$C_4$-alkyl, $C_1$–$C_4$-alkoxy, $C_2$–$C_4$-acyl, $C_1$–$C_4$-acyloxy, phenoxy, $C_2$–$C_8$-dialkylamino, halogen, nitro and cyano.

$R^1$ and $R^2$ may be:

$C_1$–$C_{20}$-alkyl, preferably $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2- dimethylpropyl, n-hexyl, isohexyl, sec-hexyl, n-heptyl, isoheptyl, n-octyl, isooctyl, particularly preferably $C_1$–$C_4$-alkyl such as methyl, ethyl, n-propyl, isopropyl, n-butyl, isobutyl, sec-butyl and tert-butyl, specifically methyl.

$C_2$–$C_{20}$-alkenyl, preferably $C_2$–$C_8$-alkenyl, such as vinyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1-ethyl-1-propenyl, 1-ethyl-2-propenyl, 1-hexenyl, 2-hexenyl, 3-hexenyl, 4-hexenyl, 5-hexenyl, particularly preferably $C_2$–$C_4$-alkenyl, specifically vinyl.

$C_2$–$C_{20}$-alkynyl, preferably $C_2$–$C_8$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, particularly preferably $C_2$–$C_4$-alkynyl, specifically propynyl.

$C_2$–$C_{20}$-acyl, preferably $C_2$–$C_4$-acyl, particularly preferably $C_2$–$C_4$-acyl such as acetyl, propionyl, butyryl and isobutyryl.

The groups mentioned above for $R^1$ and $R^2$ may be substituted by $C_1$–$C_4$-alkoxy, $C_2$–$C_4$-acyl, $C_2$–$C_4$-acyloxy, $C_2$–$C_8$-dialkylamino, halogen, nitro and/or cyano. Preferred substituted radicals are substituted alkyl radicals, particularly preferably alkyl radicals substituted by halogen, cyano and alkoxy, such as cyanomethyl, chloromethyl and methoxymethyl.

$R^1$ and $R^2$ are furthermore $C_3$–$C_8$-cycloalkyl, preferably $C_5$–$C_7$-cycloalkyl such as cyclopentyl, cyclohexyl and cycloheptyl, particularly preferably cyclohexyl, $C_4$–$C_{20}$-cycloalkylalkyl, preferably $C_4$–$C_{12}$-cycloalkylalkyl such as cyclopropylmethyl, cyclobutylmethyl, cyclopentylmethyl, cyclohexylmethyl, cyclopropylethyl, cyclobutylethyl, cyclopentylethyl, cyclohexylethyl, cyclopropylpropyl, cyclobutylpropyl, cyclopentylpropyl, cyclohexylpropyl, $C_3$–$C_8$-heterocycloalkyl, preferably a 5- or 6-membered ring which has one or two oxygen, nitrogen and/or sulfur atoms in the ring and may be aromatic or non-aromatic, such as 2- or 3-furyl, 2- or 3-thienyl, 2- or 3-pyrrolyl, 2- or 4-imidazolyl, 2- or 3-oxazolyl, 2- or 3-thiazolyl, pyridinyl, morpholyl, thiomorpholyl and pyrazolyl, $C_4$–$C_{20}$-heterocycloalkylalkyl, $C_6$–$C_{14}$-aryl, such as phenyl, 1-naphthyl, 2-naphthyl, 1-anthryl, 2-anthryl, 9-anthryl, preferably phenyl, 1-naphthyl, 2-naphthyl, particularly preferably phenyl, $C_7$–$C_{20}$-arylalkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl.

Said groups may be substituted by $C_1$–$C_4$-alkyl, $C_1$–$C_4$-alkoxy, $C_2$–$C_4$-acyl, $C_2$–$C_4$-acyloxy, $C_2$–$C_8$-dialkylamino, halogen, nitro and/or cyano.

Particularly preferred among said radicals $R^1$ and $R^2$ are aryl radicals such as phenyl, unsubstituted alkyl and acyl radicals such as methyl and acetyl, and halo- or cyano-substituted alkyl radicals such as chloromethyl and cyanomethyl.

$R^1$ and $R^2$ may furthermore be part of a saturated or mono- or polyunsaturated carbon chain having 2 to 8 carbon atoms, a cycloalkylene group having 5 to 12 carbon atoms, heterocycloalkylene group having 4 to 11 carbon atoms, an arylene group having 6 to 12 carbon atoms or a hetarylene group having 3 to 11 carbon atoms, which in each case connects the two nitrogen atoms. The alkylene, alkenylene, alkadienylene, alkatrienylene, cyclo- and heterocycloalkylene and arylene and hetarylene groups mentioned above for Y are suitable. Ethylene, vinylene and phenylene are preferred.

Further suitable catalysts are compounds of the formula II:

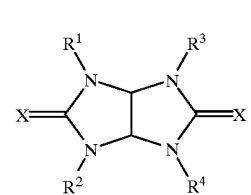

where X, $R^1$ and $R^2$ have the abovementioned meanings, and $R^3$ and $R^4$ have the meanings of $R^1$ and $R^2$, or compounds of the formula III

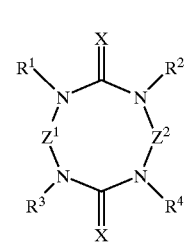

where X, $R^1$ to $R^4$ have the abovementioned meanings, and $Z^1$, $Z^2$, which may be identical or different, are methylene, ethylene or vinylene groups which are unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano. Methylene is preferred.

Some particularly suitable catalysts are listed below by way of example:
N,N-dimethylethyleneurea
N,N'-dibutylethylenethiourea
N,N'-diacetylethyleneurea
N,N'-dimethylpropyleneurea
N-chloromethyl-N'-cyanomethylpropyleneurea
N-methyl-N-ethylpropyleneurea
1,3-dimethyl-1,3-dihydrobenzimidazol-2-one
1-methyl-3-phenylimidazolidine-2,4,5-trione
1,3,4,6-tetramethyl-1,3,4,6-tetrahydroimidazo[4,5-d]imidazol-2,5-dione
4-methoxy-1-methyl-3-phenylimidazolidine-2-thione Particularly preferred catalysts are N,N'-dimethyleneurea and N,N'-dimethylpropyleneurea.

Said cyclic ureas and thioureas may be employed as such, in the form of their salts with hydrohalic acids, for example as hydrochlorides, or in the form of their salts obtainable by reaction with phosgene (Vilsmeier salts).

Thiols which can be employed in the process according to the invention are thiols having one or more SH groups. The thiols mentioned in EP-A 0 024 683 and in U.S. Pat. No. 3,299,114 are representative. $C_1$–$C_8$-Alkanethiols such as ethanethiol, ethanedithiol, butanethiol and octanethiol are particularly preferred.

The process according to the invention can be carried out as liquid-phase reaction with homogeneous catalysis. A suitable liquid reaction medium is the thiol to be employed, the thiochloroformate derived therefrom or an inert solvent or mixtures thereof.

The process according to the invention can be carried out in a melt of the thiol to be employed. To do this, the thiol is mixed with the catalyst, and phosgene is passed in. In the case of thiols which are solid at room temperature, it may be advantageous first to heat the thiol until it is liquid and then to pass in the phosgene. It may also be sufficient, in cases where, after the reaction has started, the components are liquified by the heat of the exothermic reaction, to mix the thiol and the catalyst in solid form and to pass in the phosgene. The reaction mixture can be heat of to the required temperature by external input of heat or without external input of heat utilizing the heat of reaction. Thiol and catalyst are preferably mixed in liquid form.

The novel process can also be carried out in a solvent. A particularly suitable solvent is the thiochloroformate derived from the thiol to be employed. However, it is also possible to use an additional solvent which is inert toward the thiol and phosgene and which has adequate dissolving capacity for the reactants and the catalyst. The additional inert solvent can be employed alone or mixed with the thiochloroformate. The use of an additional inert solvent may be advantageous in particular when the melting point of the thiol or of the thiochloroformate derived therefrom is above the required reaction temperature. The use of an additional inert solvent may also act to dissipate the heat of reaction. Suitable additional inert solvents are aliphatic and aromatic hydrocarbons such as pentane, hexane, cyclohexane, toluene, xylene or benzene, halogenated hydrocarbons such as trichloroethane, chlorobenzene or dichlorobenzene, or esters such as ethyl acetate or butyl acetate.

The novel process is preferably carried out in a melt of the thiol to be employed or in the thiochloroformate derived therefrom as solvent, without using an additional inert solvent.

The novel process can be carried out continuously or batchwise. The novel process is preferably carried out continuously, for example in a stirred vessel, in a cascade of stirred vessels, in a loop reactor or in a countercurrent column, The reaction is generally carried out at from −20 to 180° C., preferably 0 to 120° C., particularly preferably 20 to 80° C., specifically 45 to 65° C. The reaction is generally carried out under pressures of from 0.01 to 50 bar, preferably 0.5 to 5 bar, particularly preferably under atmospheric pressure.

The catalyst is generally employed in amounts of from 0.01 to 2 mol % based on the amount of thiol employed. The amount of the catalyst also depends on whether the reaction is carried out in the thiol alone or in the presence of solvent. The amount of catalyst used is often so low that it is unnecessary to remove the catalyst from the reaction product. It is preferably from 0.02 to 1 mol %, particularly preferably from 0.02 to 0.1 mol %. Particularly small amounts of catalyst can be employed when the thiol is reacted in the melt without use of solvent. The amount of catalyst used can thus be below 0.05 mol %.

The molar ratio of phosgene to thiol is generally from 0.5:1 to 50:1. An excess of phosgene will normally be used because, otherwise, unreacted thiol would remain. In addition, an excess of thiol favors side reactions such as the formation of dithiocarbonates from thiol and previously formed thiochloroformate. Otherwise, a large excess of phosgene (for example more than 2:1) has no other advantage. The molar ratio of phosgene to thiol is therefore preferably 1:1 to 2:1, particularly preferably 1:1 to 1.5:1, in particular 1:1 to 1.2:1.

Very high thiochloroformate yields can be obtained by the novel process. Thus, the thiochloroformate yield based on thiol employed is generally more than 98 mol %, preferably more than 99 mol %. The yield may be more than 99.5 mol %.

The phosgenation can be followed by one or more steps for purifying the reaction product. Thus, it is possible where appropriate for the liquid discharge from the phosgenation to be freed of insoluble impurities by a mechanical separation such as clarifying filtration. A mechanical separation step of this type is often sufficient to obtain a product of sufficiently high purity, and further workup can be omitted. However, further purification steps to remove soluble impurities, for example distillation or recrystallization, may follow.

The thiochloroformate which is formed has very high purity. The purity of the crude product is generally >98 mol %, preferably >99 mol %. Purities of >99.5 mol % may be obtained. The crude product is intended to mean the reaction mixture after carrying out the reaction, where appropriate after carrying cut a mechanical separation, but before carrying out further purification steps to remove soluble impurities. The purity is intended to mean the thiochloroformate content of the reaction mixture which, when a solvent is used, is based only on that part of the reaction mixture which was not solvent at the start of the reaction.

Additional components which the crude product may contain are the catalyst, byproducts and unreacted thiol. Byproducts are, for example, dithiocarbonates and disulfides. The amount of dithiocarbonate in the crude product is generally <1 mol %, preferably <0.5 mol %, particularly preferably <0.1 mol %. The amount of disulfide in the crude product is generally <0.5 mol %, preferably <0.1 mol %, particularly preferably <0.01 mol %. The amount of unreacted thiol is generally <0.1 mol %, preferably 0.01 mol %. The % data are based, when a solvent used, on that part of the reaction mixture which was not solvent at the start of the reaction.

The novel process is advantageous in that the reaction takes place substantially completely and with high selectivity under comparatively mild conditions and in the presence of very small amounts of catalyst. The discharges from the reaction may be caused because of the very small content of additional components. This may make workup of the crude product unnecessary.

The invention is explained in detail by the following examples.

EXAMPLES 1 AND 2 AND COMPARATIVE EXAMPLES C1–C4

A 1.1-fold excess, based on octanethiol, of phosgene was passed into a mixture of n-octanethiol and X mol of catalyst in the molar ratio 1 :X at T° C. over the course of t hours. The mixture was then kept at the reaction temperature for a further hour. Thereafter excess phosgene and remaining hydrogen chloride were blown out of the mixture with nitrogen. The resulting crude product was clarified by filtration and then investigated by gas chromatography. Comparative Examples C1 and C2 were carried out as disclosed in DE-A 41 37 012, Comparative Example C3 as in EP-A 0 053 981 and Comparative Example C4 as in EP-A 0 024 683.

Details of these experiments are to be found in the following table. It is possible by the novel process to reduce the content of additional components to one fifth that in prior art processes.

| Example | Catalyst | X | T (° C.) | t(h) | GC analysis (% area) | | | | APHA: color number or color |
|---|---|---|---|---|---|---|---|---|---|
| | | | | | Chloroformate | Thiocarbonate | Disulfide | Thiol | |
| 1 | Dimethyl-propylene- urea | 0.0005 | 55 | 4 | 99.8 | 0.04 | 0.01 | 0.00 | 6 |
| 2 | Dimethyl-ethylene- urea | 0.0005 | 55 | 4 | 99.8 | 0.05 | 0.00 | 0.00 | 8 |
| V 1[1)] | Trioctyl-phosphine oxide | 0.001 | 80 | 1 | >99 | 0.1 | no information | 0.00 | yellow |
| V 2[2)] | Triphenyl phosphite | 0.002 | 80 | 4 | 98.1 | 0.3 | no information | 0.7 | yellow |
| V 3[1)] | Tetrabutyl- urea | 0.007 | 30 | 4 | 98.2 | 0.4 | 0.6 | no information | no information |
| V 4[3)] | Dimethyl-formamide | 0.002 | 50 | no information | 99.0[4)] | no information | no information | no information | almost colorless[4)] |

[1)] Example taken from DE-A 41 37 012
[2)] Example taken from EP-A 00 53 981
[3)] Example taken from EP-A 00 24 683
[4)] After distillation

We claim:

1. A process for preparing thiochloroformates by reacting thiols with phosgene in the presence of a catalyst, wherein the catalyst is selected from a cyclic urea or a cyclic thiourea which may be in the form of a salt obtainable by reaction with a hydrohalic acid or phosgene.

2. The process as claimed in claim 1, wherein the catalyst used is a compound of the formula I

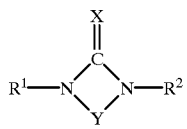

(I)

where

X is an oxygen or sulfur atom,

Y is a saturated or mono- or polyolefinically unsaturated carbon chain which has 2 to 8 carbon atoms and which is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and cyano and which may contain an ether, thioether, tertiary amino, keto, lactone, alkyl-substituted lactam, sulfone or diketo moiety, or is a cycloalkylene having 5 to 12 carbon atoms, heterocycloalkylene group having 4 to 11 carbon atoms, arylene group having 6 to 12 carbon atoms or hetarylene group having 3 to 11 carbon atoms, each of which is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and cyano, and $R^1$ and $R^2$, which may be identical or different, are $C_1$–$C_{20}$-alkyl, $C_2$–$C_{20}$-alkenyl or $C_2$–$C_{20}$-alkynyl, each of which is unsubstituted or mono- to tri-substituted by $C_1$–$C_4$-alkoxy, $C_2$–$C_4$-acyl, $C_2$–$C_4$-acyloxy, $C_2$–$C_8$-dialkylamino, halogen, nitro and/or cyano, or is $C_2$–$C_{20}$-acyl or is $C_3$–$C_8$-cycloalkyl, $C_4$–$C_{20}$-cycloalkylalkyl, $C_3$–$C_8$-heterocycloalkyl, $C_4$–$C_{20}$-heterocycloalkylalkyl, $C_6$–$C_{14}$-aryl or $C_7$–$C_{20}$-arylalkyl, each of which is unsubstituted or mono- to trisubstituted by $C_1$–$C_4$-alkyl, $C_1$–$C_4$-alkoxy, $C_2$–$C_4$-acyl, $C_2$–$C_4$-acyloxy, $C_2$–$C_8$-dialkylamino, halogen, nitro and/or cyano, or $R^1$ and $R^2$ are part of a mono- or polyolefinically unsaturated carbon chain having 2 to 8 carbon atoms, a cycloalkylene group having 5 to 12 carbon atoms, heterocycloalkylene group having 4 to 11 carbon atoms, arylene group having 6 to 12 carbon atoms or hetarylene group having 3 to 11 carbon atoms, which in each case connects the two nitrogen atoms, and/or a compound of the formula II

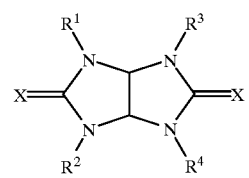

(II)

where X, $R^1$ and $R^2$ have the abovementioned meanings, and $R^3$ and $R^4$ have the meanings of $R^1$ and $R^2$, or a compound of the formula III

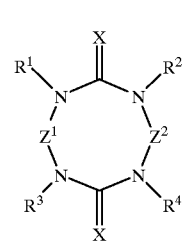

(III)

where X, $R^1$ to $R^4$ have the abovementioned meanings, and $Z^1$, $Z^2$, which may be identical or different, are methylene, ethylene or vinylene groups which are unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano.

3. The process as claimed in claim 1, wherein N,N'-dimethylpropyleneurea or N,N'-dimethylethyleneurea is used as catalyst.

4. The process as claimed in claim 1, wherein $C_1$–$C_8$-alkanethiols, $C_4$–$C_8$-cycloalkanethiols, $C_6$- and $C_{12}$-arylthiols, $C_7$–$C_{12}$-aralkylthiols and/or $C_3$–$C_{12}$-heterocycloalkylthiols are reacted.

5. The process as claimed in claim 1, wherein from 0.02 to 1 mol % of the catalyst is employed per equivalent of thiol.

6. The process as claimed in claim 1, wherein the reaction is carried out at from 20 to 80° C. under atmospheric pressure.

7. The process as claimed in claim 1, wherein the reaction is carried out in the melt of the thiol.

8. The process as claimed in claim 1, wherein the reaction is carried out in the presence of a solvent.

9. The process as claimed in claim 8, wherein the thiochloroformate derived from the thiol employed is used as solvent.

* * * * *

UNITED STATES PATENT AND TRADEMARK OFFICE
CERTIFICATE OF CORRECTION

PATENT NO.: 6,162,939

DATED: December 19, 2000

INVENTOR(S): WEYER et al.

It is certified that error appears in the above-identified patent and that said Letters Patent is hereby corrected as shown below:

In the abstract, line 2, after "phosgene" insert --in the presence of a catalyst--.

Signed and Sealed this

Twenty-ninth Day of May, 2001

*Attest:*

NICHOLAS P. GODICI

*Attesting Officer*  *Acting Director of the United States Patent and Trademark Office*